United States Patent [19]
Voelker

[11] 3,994,284
[45] Nov. 30, 1976

[54] FLOW RATE COMPUTER ADJUNCT FOR USE WITH AN IMPEDANCE PLETHYSMOGRAPH AND METHOD

[75] Inventor: Scott F. Voelker, Lafayette, Calif.

[73] Assignee: Systron Donner Corporation, Concord, Calif.

[22] Filed: Dec. 31, 1975

[21] Appl. No.: 645,936

[52] U.S. Cl. .................. 128/2.05 F; 128/2.05 V; 128/2.1 Z; 235/151.34
[51] Int. Cl.² .......................................... A61B 5/02
[58] Field of Search ............ 128/2.05 F, 2.05 V, 128/2.05 R, 2.1 Z; 235/151.34, 194, 183

[56] References Cited
UNITED STATES PATENTS

| 2,700,135 | 1/1955 | Tolles | 235/194 X |
| 3,167,649 | 1/1965 | Walp | 235/194 |
| 3,433,935 | 3/1969 | Sherman | 235/151.34 X |
| 3,445,643 | 5/1969 | Schmoock et al. | 235/194 |
| 3,651,318 | 3/1972 | Czekajewski | 235/183 |
| 3,730,171 | 5/1973 | Namon | 128/2.05 Z |
| 3,835,839 | 9/1974 | Brown | 128/2.05 F |

Primary Examiner—Kyle L. Howell
Attorney, Agent, or Firm—Flehr, Hohbach, Test, Albritton & Herbert

[57] ABSTRACT

A computer adjunct is described which is used in combination with an impedance plethysmograph. The impedance plethysmograph provides signals related to conductance in a biological segment and related to deviation from a quiescent resistance level in the biological segment as body fluids are pumped therethrough in a pulsatile manner by the pumping action of the heart. The deviation of the segment resistance contains artifact signals such as those imposed by movement or breathing. The computer adjunct contains means for providing a signal indicative of heart pumping rate and circuit means for measuring the level of the artifact signals once each heart pumping cycle and generating a correction signal related thereto. The correction signal is thereafter applied to the deviation signal for reducing error induced by the artifact signals. The heart rate signal is conditioned to obtain a signal related thereto which is averaged. The corrected deviation signal is also averaged. The averaging is performed by circuitry which integrates the corrected deviation signal, thereby reducing residual cyclic noise due to the artifact signal while still affording relatively short output stabilization time. The two averaged signals are multiplied together and then combined with the segment conductance signal for providing an output signal indicating blood flow rate through the biological segment. The combination is capable of blood flow rate measurements for calf segments or thoracic segments.

12 Claims, 3 Drawing Figures

FLOW RATE COMPUTER ADJUNCT FOR USE WITH AN IMPEDANCE PLETHYSMOGRAPH AND METHOD

BACKGROUND OF THE INVENTION

The flow rate computer adjunct relates to conversion of impedance plethysmograph information to usable clinical data, and more particularly to the transposition of biological segment conductance, impedance deviation, and heart pumping rate signals to an output signal indicating blood flow rate which is relatively free of artifact errors.

Impedance plethysmography is a non-invasive, analog analysis of body mechanical activity which depends upon the electrical prpoerties of the body tissue. An impedance plethysmograph and flow rate computer adjunct and method is described in U.S. Pat. No. 3,835,839, assigned to the assignee of the instant invention. The combination disclosed therein includes a DC restorer for returning the signal indicative of deviation from biological segment basic resistance to a zero reference at the beginning of each deviation cycle. This technique was utilized in an attempt to remove artifact errors from the deviation signal. While some error was removed thereby, a large error still remained and output signal stability was such as to severely limit the use thereof.

As further described therein tissue segment blood flow rate determination has previously been accomplished by graphically recording plethysmograph output. A wave shape proportional to the deviation in biological segment volume, and thus flow rate, was used. Blood flowing through the arterial system into the segment flows away from the segment due to venous runoff. Since runoff is occurring simultaneously with arterial inflow, the entire volume of blood pumped through the segment during one heart pumping cycle is not present in the segment at one time. Therefore, the graph of volumetric deviation within the segment does not directly indicate the maximum volume of flow through the segment for each heart pump cycle. The volume of flow within the segment builds up relatively rapidly at the beginning of the pumping cycle and then begins to trail off as venous runoff begins to occur. There is a primary slope on the trailing edge of the graphical recording of the pumping cycle which has an average negative slope. Extending the average negative slope to a point where it intersects the ordinate drawn through the beginning of the pulse, provides an extrapolated value which theory and practice have shown to represent a quantity proportional to the true volumetric flow through the segment for each heart pumping cycle. Attempts other than that described in U.S. Pat. No. 3,835,839 mentioned above have been made to perform the graphical extrapolation electronically. These attempts have proven unsatisfactory because of interfering noise levels and, in the apparatus and method disclosed in the above-referenced patent, because of the presence of artifact signals as discussed above. There is, therefore, a need for an apparatus and method for measuring blood flow rate through a biological segment which provides a stable output signal and reduction of noise induced output signal error.

SUMMARY AND OBJECTS OF THE INVENTION

The flow rate computer adjunct disclosed herein is useful with an impedance plethysmograph having electrodes which are applied in a conventional manner to a biological segment having pulsatile biologic fluid flow passing therethrough. Signals are provided by the impedance plethysmograph which are indicative of tissue conductance and deviation from a reference tissue conductance in the biological segment. The deviation signal contains artifact signals such as those induced by breathing or movement. The computer adjunct further includes means for providing a first cyclic signal which is indicative of the pulsatile biologic fluid flow and means for receiving the first cyclic signal and thereby generating a second cyclic signal having an initial signal portion and a terminal signal portion. Means is provided responsive to the initial portion of the second cyclic signal for sensing instantaneous magnitude of the artifact signal in the deviation signal and for producing a correction signal corresponding to the instantaneous magnitude. The correction signal is applied to the signal indicative of deviation by means responsive to the terminal portion of the second cyclic signal for obtaining a corrected deviation signal. The first cyclic signal is directed to circuitry for providing a signal of predetermined magnitude and dwell time synchronous therewith. The corrected deviation signal and the synchronous signal are each averaged and multiplied together to obtain a product signal. The product signal is connected to circuit means for multiplication thereof by a constant signal of magnitude determined by biologic segment electrical characteristics and placement of the plethysmograph electrodes on the segment. The last resulting product signal is multiplied by the tissue conductance signal for providing an output signal indicative of the flow rate of biologic fluid through the biologic segment.

In general it is an object of the computer adjunct for use with the impedance plethysmograph to convert plethysmograph to a direct indication of blood flow rate in volumetric units per unit of time.

Another object of the computer adjunct for use with the impedance plethysmograph is to provide such an output signal which is stable and indicates a measurement within a short time after the measured event occurs.

Another object of the computer adjunct for use with the impedance plethysmograph is to provide a blood flow rate indicative output signal which is substantially free of artifact output error.

Additional objects and features of the invention will appear from the following description in which the preferred embodiments have been set forth in detail in conjunction with the accompanying drawings.

DESCRIPTION OF THE PREFERRED EMBODIMENT

In the invention described herein particular characteristics of a biological segment are measured and presented in the form of electrical signals related thereto, and the signals are treated in the circuitry of the invention to produce intelligible, error corrected, clinical data.

The terms "thoracic segment" and "calf segment" are defined for use herein as referring generally to segments including portions of the respiratory system and segments not including such portions respectively.

Figure 1:
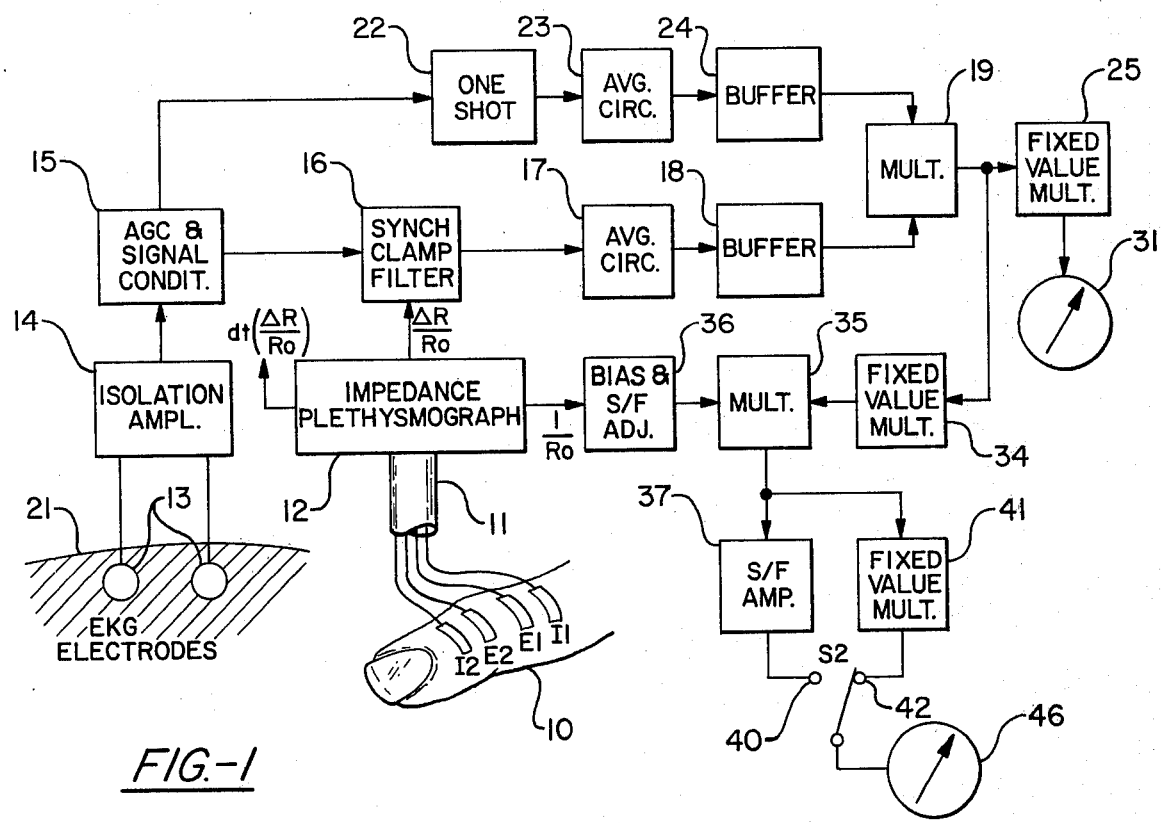
FIG. 1 is a block diagram of the computer adjunct used with an impedance plethysmograph showing signal processing for calf and thoracic segment flow rate indications.

Referring to FIG. 1, electrode pairs I1 and E1, and I2 and E2 are seen applied to a biological segment represented by finger 10. Conductors for the electrode pairs are generally indicated at 11 and connect the electrode pairs to an impedance plethysmograph 12. The impedance plethysmograph 12 may be, but is not necessarily, the type described in U.S. Pat. No. 3,882,851. Output signals are generated by the plethysmograph 12 which are proportional to the conductance $1/R_0$, the deviation from basic resistance $\Delta R/R_0$, and the time derivative of the deviation, $dt(\Delta R/R_0)$ of the biologic segment having a length L. In this embodiment the latter signal may or may not be used to provide a signal indicative of heart pumping rate. As shown in FIG. 1 the signal indicative of heart pumping rate is obtained through the use of an electrocardiogram (EKG) device having electrodes 13 for sensing heart pumping rate connected to an isolation amplifier 14 for providing an EKG output therefrom which is a cyclic signal indicating heart pumping rate.

The signal processing for producing an output which is meaningful in clinical analysis is accomplished as follows. The signal proportional deviation, $\Delta R/R_0$, is directed to a synchronous clamp filter 16. The EKG signal is connected to an automatic gain control (AGC) and signal conditioning network 15. The conditioned EKG signal is also connected to synchronous clamp filter 16 for providing a correction to the deviation signal as hereinafter described. The corrected deviation signal is connected to an averaging circuit 17 which provides integration of the corrected deviation signal. The integration performs a filtering function for the corrected deviation signal, thereby removing residual artifact cyclic noise therefrom. A buffer circuit 18 is provided to receive the averaged corrected deviation signal and to provide an output connected to a multiplier 19. The conditioned EKG signal from AGC and signal conditioning circuit 15 is connected to a one shot multivibrator 22. The conditioned signal is used because it provides a sharp definable pulse as an input to multivibrator 22. A square pulse output from multivibrator 22 is connected to an averaging circuit 23. The average DC level of the multivibrator output is connected to a buffer 24 which is substantially the same as buffer 18. The output from buffer circuit 24 is delivered to the multiplier 19 which produces an output representing the product of the average corrected deviation signal and the averaged output from multivibrator 22. This product of the averaged signals is connected to a fixed value multiplier 25 producing an output connected to a meter indicator 31 for the purpose of indicating normalized thoracic biologic fluid flow rate.

The product of the averaged signals is also directed to a second fixed value multiplier 34 which is connected to a multiplier 35. The signal proportional to conductance is connected to a bias and scale factor adjust network 36 producing output which also is directed to multiplier 35. The product output of multiplier 35 is directed to a scale factor amplifier 37 which produces an output connected to a first terminal 40 of the switch S2. The product output of multiplier 35 is also directed to a third fixed value multiplier 41 which produces an output connected to a second terminal 42 on switch S2. A movable contact 43 on switch S2 is connected to a meter indicator 46 for providing absolute or normalized biologic fluid flow rates through the biologic segment as selected by switch S2.

The term $R_0$ represents the basic impedance or resistance of a biologic segment. It is the quiescent resistance of the tissue and bone within the segment. The equivalent circuit of the biological segment at peak diastole is represented by the quiescent resistance $R_0$. The equivalent circuit at peak systole is represented by the parallel combination of $R_0$ and the electrical resistance $R_B$ of the small volume of blood which is pumped into the biologic segment at peak systole. The quantity represented by the difference between $R_0$ and the parallel combination resistance is defined as $\Delta R$. By assuming that $R_B$ is very great in comparison to $R_0$ the relationship $R_B = R_0^2/\Delta R$ is obtained.

The standard equation for electrical resistance of any material is $\rho L/A$ where $\rho$ is the resistivity, L is the length of the material and A is a cross sectional area. Multiplying this last relationship by L/L which is unity, the relationship $\rho L^2/V$ results, where V is the total volume. Transposing V and R, the relationship $\rho L^2/R$ arises where R is the total resistance of the biological segment. Change in resistance of the biological segment is brought about by variation in the quantity $R_B$ which is in turn dependent upon the change in volume within the biologic segment during one heart pumping cycle. Thus the following relationship is valid: $\Delta V = \rho L^2/R_B$.

The last formula set forth above provides a relationship between change in volume and change in resistance within a biological segment. The flow rate in terms of volumetric units per unit of time is obtainable by multiplying the change in volume for each heart pumping cycle by the number of heart pumping cycles per unit of time. The number of heart pumping cycles per unit of time is refereed to as the heart rate, $H_R$. The following relationships result where the unit of time is 1 minute:

$$\Delta V/\text{minute} = \Delta V \times H_R$$

$$= (\rho L^2/R_B) \times H_R$$

$$= (\rho L^2)/(R_0 2/\Delta R) \times H_R$$

$$= \rho L^2 H_R \Delta R/R_0^2$$

The last above relationship is a hydraulic flow rate which contains only known factors or factors supplied by the impedance plethysmograph outputs and the conditioned EKG signal.

Figure 3:
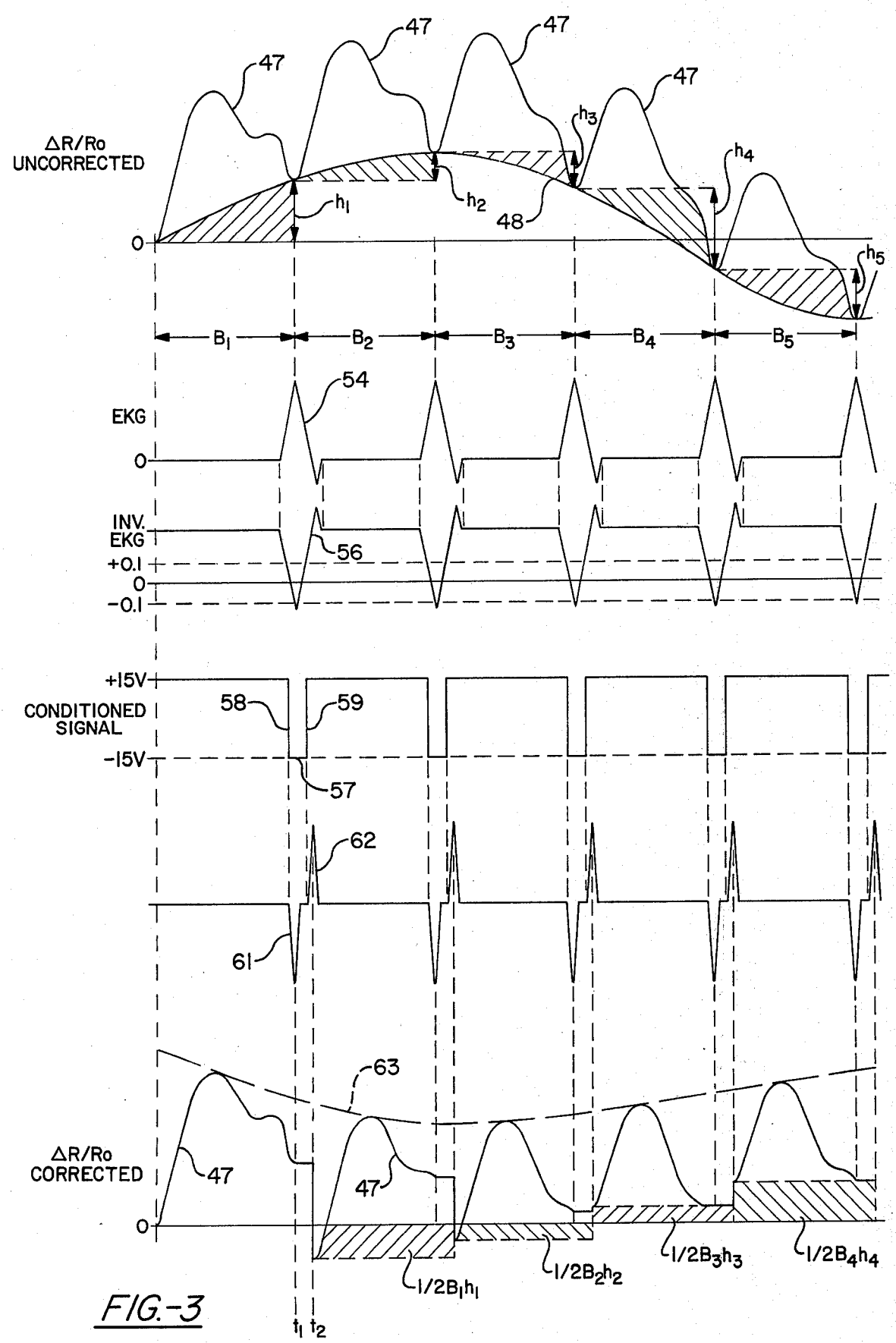
FIG. 3 is a timing diagram showing the manner in which the circuit of FIG. 2 corrects for artifact error.

Referring to the upper portion of FIG. 3, a series of pulses 47 are shown representing deviation from basic or quiescent resistance, $\Delta R/R_0$, in a biological segment such as finger 10. Pulses 47 are riding on top of an artifact wave 48 which may be produced by breathing or movement of the subject of which the biologic segment is a part. The amplitudes of deviation waves 47 and artifact wave 48 are shown in approximate one to one proportion for the purposes of this explanation, but in fact the artifact wave 48 has an amplitude which is generally four to five times that of deviation wave 47. With the consequent possibility of a 5:1 noise ratio, it is apparent that without some treatment of the combined deviation and artifact signals to eliminate the artifacts, it will be extremely difficult to gain intelligible data from the combined signal by which to obtain a measurement of blood flow through the biologic segment.

Figure 2:
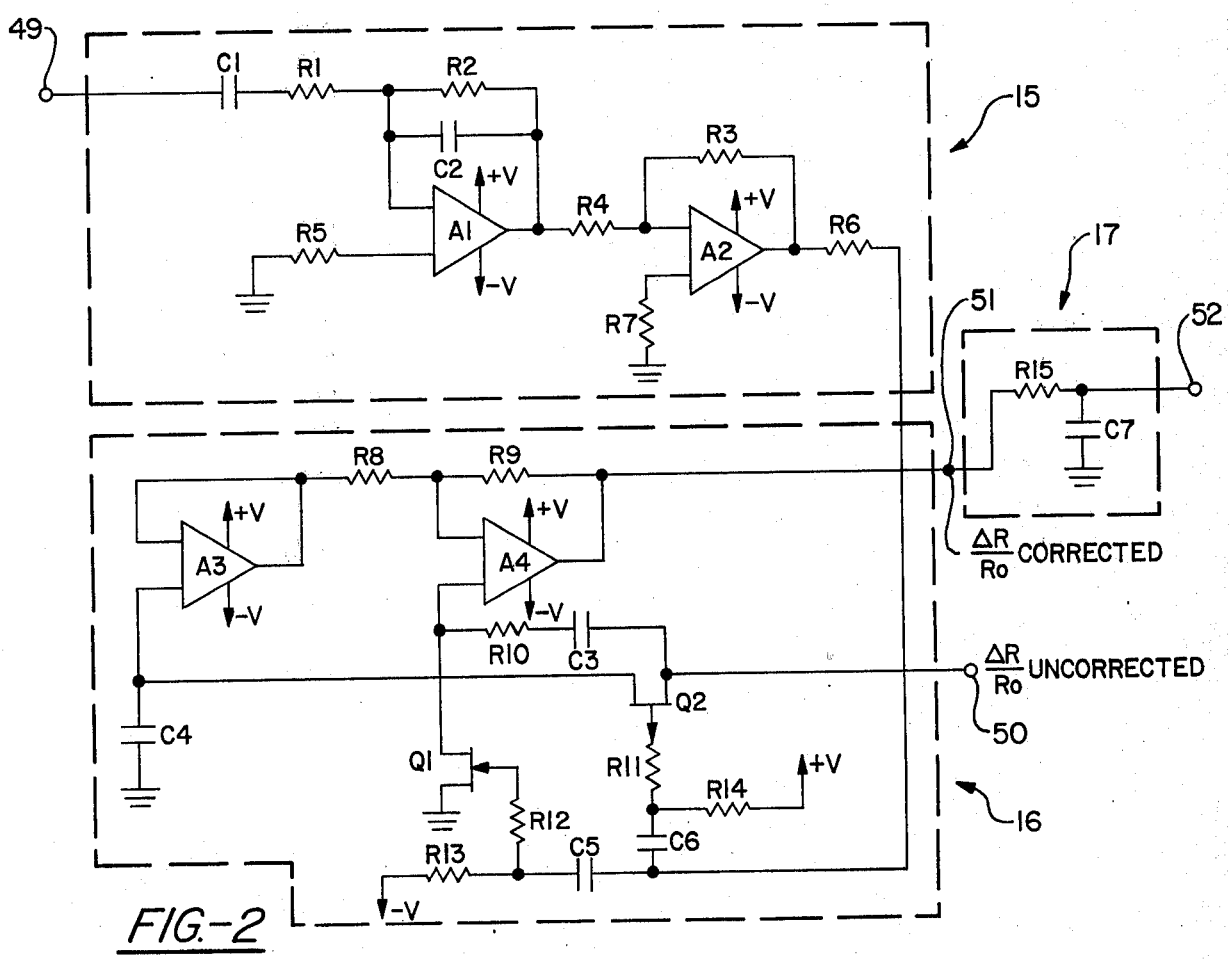
FIG. 2 is a schematic diagram of the automatic gain control and signal conditioner, the synchronous clamp filter and an averaging circuit used in the invention.

Turning now to FIG. 2, the electrical schematic for AGC and signal conditioning circuit 15, synchronous filter 16 and a simple averaging circuit 17 is shown. The EKG signal from isolation amplifier 14 is connected to an input terminal 49 on signal conditioner 15. The EKG signal is inverted and provided with a new reference by amplifier A1 and circuitry associated therewith as seen in FIG. 2. The output signal from amplifier A1 is connected to the input of device A2 which provides an output having a predetermined dwell time and having an initial and a terminal portion. The output from device A2 is connected to the input of the synchronous clamp filter which also has connected thereto at terminal 50, the uncorrected deviation wave 47, $\Delta R/R_0$, combined with the artifact wave 48. The combined deviation and artifact signal is connected to the source of a field effect transistor Q2. The output from device A2 is coupled to the gate of transistor Q2 and the gate of field effect transistor Q1 through associated circuitry as shown. The initial portion of the output from device A2 turns on transistor Q2 causing the amplitude of the artifact wave 48 to be measured at capacitor C4, and the terminal portion of the output from device A2 cause transistor Q1 to be actuated to adjust the output from amplifier A4 to a level dependent upon the measured amplitude of the error inducing artifact wave 48. An output is produced at terminal 51 which is the corrected deviation wave having most of the artifact error removed therefrom. Some error remains on the corrected deviation output signal at terminal 51 due to reasons hereinafter explained.

Averaging circuit 17 is connected to output terminal 51 for receiving the corrected deviation signal and for reducing the noise error remaining in the corrected deviation signal. The filtered or averaged corrected deviation signal is presented at output terminal 52 for connection to buffer circuit 18 and subsequent signal processing as described above.

Turning now to FIG. 3, it may be seen that deviation signal 47 contains that portion of artifact wave 48 thereunder during the first cycle of signal 47 having a period designated $B_1$. Presuming the artifact signal 48 has a shape somewhat similar to a sine wave, the area under the first cycle of deviation signal 47 is seen to approximate a right triangle having a base B1 and an altitude $h_1$. In terms of area under the first cycle of deviation signal 47 the error induced by artifact signal 48 is ½ $B_1 h_1$. This error is measured and a compensation equivalent thereto is forced upon the subsequent cycle of deviation signal 47. Since the error ½ $B_1 h_1$ is added to the first cycle of deviation wave 47 as seen in the upper portion of FIG. 3, it is subtracted from the subsequent cycle of deviation signal 47 seen as the second cycle of signal 47 in the bottom portion of the timing diagram. In like manner the area of the right triangle having a base $B_2$ and an altitude $h_2$ in the upper sequence is measured and applied as a correction to the third cycle of deviation signal 47 in the bottom sequence. The third cycle of deviation wave 47 may be seen to have an error represented by ½ $B_3 h_3$ which for the period $B_3$ is decreasing the area under deviation wave 47. Consequently the compensation must be added to the subsequent or fourth cycle of deviation wave 47, which is seen to be the case in the bottom portion of FIG. 3. In like manner, the error in each cycle of deviation signal 47 due to artifact signal 48 is measured and the sense of the error detected. A correction signal is generated thereby and applied to the subsequent cycle of deviation signal 47.

The manner in which the above is accomplished will not be reviewed by reference to FIGS. 2 and 3 together. The combined deviation signal and artifact signal uppermost in FIG. 3 is obtained from the impedance plethysmograph 12 and connected to input terminal 50 on synchronous clamp filter 16 as mentioned above. The EKG signal connected to terminal 49 on signal conditioner 15 is seen as EKG wave 54 in FIG. 3. EKG wave 54 is inverted and the zero reference adjusted to provide the output from amplifier A1 seen as wave 56 in FIG. 3. Device A2 is configured to produce square wave 57 therefrom having an initial or leading edge 58 and a terminal or trailing edge 59 with a predetermined dwell time therebetween. Leading edge 58 is generated when inverted EKG wave 56 passes in a descending direction through a predetermined voltage level, in this instance +0.1 volts. Trailing edge 59 is generated as inverted EKG wave 56 passes in an ascending direction through the predetermined voltage. Square wave 57 initiates a spike 61 by momentarily turning on FET Q2 which measures the instantaneous magnitude of artifact wave 48. The trailing edge 59 of square wave 57 momentarily turns on FET Q1 to adjust the output from amplifier A4 to reflect the measured error. Thus measuring of the artifact error takes place at time $t_1$ and application of the correction to the subsequent cycle of deviation signal 47 takes place at time $t_2$. The error in one cycle of deviation signal 47 is therefore compensated in the subsequent cycle thereof.

The resulting corrected deviation signal lowermost in FIG. 3 is seen to have a peak variation represented by dashed line 63, due in part to the approximation nature of computing the error induced in the deviation wave 47 by artifact wave 48, and also due in part to the fact that the correction for error computed in one cycle of deviation wave 47 is not applied until the subsequent cycle. Some cyclic noise signal is still present, therefore, even in the corrected wave of FIG. 3. Tests show that the aforementioned 5:1 noise to signal ratio imposed by the artifact wave in the uncorrected deviation signal is reduced to an approximate 20% noise content or 1:5 noise to signal ratio in the corrected deviation wave seen in FIG. 3. The noise signal represented by dashed line 63 has a frequency similar to that of artifact wave 48. Averaging circuit 17 is provided for providing an integration of the signal lowermost in FIG. 3. The output from averaging circuit 17 is in the form of a signal level with a reduction of noise level therein from the 20% level to an approximate 1% level. The simplest circuit 17 utilizes first order RC filter configured as shown by R15 and C7 of FIG. 2. As an example the predominant artifact signal may have a period of about 3 seconds. In such a case, a circuit 17 having a 10 second time constant and a corner frequency of 1/60 hertz with 20:1 attenuation at 166 hertz is obtained when R15 equals 1 megohm and C7 equals 1 microfarad. Such a configuration would provide a readable output at terminal 52 with 10 seconds of the occurance of the measured signal, assuming a zero level initial condition at the time of signal occurance. This is clearly a worst case condition, and accurate signal indication is available after a shorter period of time for any other signal initial condition levels. It should also be noted that the first order RC filter configuration of circuit 17 is but an example, and interacting filters more complex than that represented by R15 and C7 may be utilized to provide shorter output signal response time to blood flow conditions. It should further be noted that the 1% noise to signal ratio is more than adequate for the applications discussed herein, because physiological variables cause deviation signal variations in excess of 1%, as a general rule.

Turning now to the operation of the impedance plethysmograph 12 and the flow rate computer adjunct for use therewith, reference is again made to FIG. 1. The computation utilizing the output signals from the impedance plethysmograph 12, corrected as described above, is based on the principle that the average value of the deviation wave form 47 in FIG. 3 is proportional to the blood flow for each heart pumping cycle. The combined signal proportional to biological segment resistance deviation 47, $\overline{\Delta R}/R_0$, combined with artifact signal 48, serves as one input to synchronous clamp filter 16 as described above. The conditioned EKG signal 57 from signal conditioner 15 is also connected to synchronous clamp filter 16, which provides an output coupled to averaging circuit 17 as hereinbefore described. Consequently, a relatively clean corrected and averaged deviation signal 47 is presented to buffer circuit 18 in the form of a DC voltage proportional to $\Delta R/R_0$. Buffer 18 is provided in the circuit to prevent loading of the averaging circuit 17 by subsequent stages in the computer adjunct.

Either the time derivative of the deviation signal $dt(\Delta R/R_0)$, or the conditioned EKG signal from signal conditioner 15 is connected to the one shot multivibrator 22 which provides a clear pulse output having a defined pulse width each time it is triggered by one of the forementioned signals. Multivibrator 22 is therefore triggered once each heart pumping cycle. Recurrance rate of pulses from multivibrator 22 is therefore indicative of the heart rate, $H_R$, and the pulses are averaged in the averaging circuit 23 to provide a DC voltage which is directly proportional to heart rate. Buffer 24 is provided to prevent loading of the averaging circuit 23 by subsequent stages in the computer 13. The two DC voltages proportional to deviation and heart rate are multiplied in multiplier 19 providing an output proportional to the relationship $\Delta R H_R/R_0$. Fixed value multiplier 34 has a gain determined by biological segment electrical characteristics and electrode pair placement, which in this embodiment is equivalent to $\rho L^2 \Delta R H_R/R_0$ to multiplier 35. The conductance signal, $1/R_0$ from the plethysmograph 12 is adjusted for bias and scale factor at 36 and is also directed to multiplier 35. The output from multiplier 35 is therefore $\rho L^2 \Delta R H_R/R_0^2$. This is seen to be the quantity computed above for $\Delta V$/minute, which is hydraulic flow volume through the biologic segment per unit of time.

The computer output is presented in two forms to represent segment flow rate. A scale factor amplifier 37 is provided to enable calf segment flow rate indicator 46 to indicate absolute flow rate in desired volumetric units per unit of time. Absolute flow rate units may be milliliters per minute in this instance. Moving contact 43 on switch S2 is moved to terminal 40 to produce this indication on the meter 46.

The output of multiplier 35 is also directed to a fixed value multiplier 41 which in this embodiment has a gain equivalent to 100/V. When the moving contact 43 is positioned to contact 42 at switch S2, the segment flow rate indicator 46 indicated normalized flow rate in volumetric units per unit of time per volumetric unit of biologic segment. Normalized flow rate units in this instance may be milliliters per minute per 100 milliliters.

Special treatment has empirically been found to be justified when the plethysmograph 12 is utilized to measure thoracic segments. The thoracic segment volume may be expressed as follows: $V = \rho L^2/R_0$. Using the expression derived above for hydraulic flow rate and substituting the last expression for volume the following results:

$$\Delta V/\min/V/100 = \rho L^2 \Delta R H_R/R_0^2 V/100 = \rho L^2 \Delta R H_R 100/(R_0^2 \rho L^2)/R_0 = 100 \Delta R H_R/R_0$$

It is apparent that the output of multiplier 19 is equivalent to the last expression above without the factor of 100. Fixed value multiplier 25 provides a gain of 100 for the input signal coming from multiplier 19, thus providing a normalized thoracic flow rate which is indicated on the thoracic flow rate read out meter 31. The constant or factor 100 arises in this embodiment because the normalized flow rate is expressed in milliliters per minute per 100 milliliters of thoracic segment.

It should be noted that the segment volumetric measurement for calf segment data must be determined geometrically. Once this is done a manual adjustment may be made at fixed value multiplier 41 to provide a normalized flow rate indications at the calf segment flow rate meter 46. Normalized thoracic flow rate indications on indicator 31 on the other hand, are more easily provided. Since thoracic volume segments are found empirically to be equivalent to the quantity $\rho L^2/R_0$, normalized thoracic flow rates do not require geometric measurement of thoracic segment volumes and subsequent manual adjustment.

A computer adjunct is provided for use with an impedance plethsymograph which supplies clinical data relative to volumetric blood flow, variations to blood flow volume, and venous runoff hindrance within a matter of seconds after the physiological event has occurred. The technique is nontraumatic to the biological segment under observation, and provides for measurement of absolute and normalized flow rates through the segment. Normalized flow rate measurements have the added advantage of providing comparative clinical data from a number of patients.

What is claimed is:

1. A flow rate computer adjunct for use with an impedance plethysmograph having electrodes applied to a biologic segment having pulsatile biologic fluid flow therethrough, the impedance plethysmograph providing signals indicative of tissue conductance and deviation from a reference tissue conductance in the biologic segment, the signal indicative of deviation containing artifact signals, comprising means for providing a first cyclic signal indicative of the pulsatile biologic fluid flow, means for receiving said first cyclic signal providing a second cyclic signal having an initial and a terminal portion, means responsive to said initial portion of said second cyclic signal for sensing the instantaneous magnitude of the artifact signal and producing a correction signal corresponding thereto, means responsive to said terminal portion of said second cyclic signal for applying said correction signal to the signal indicative of deviation thereby obtaining a corrected deviation signal, means for averaging said corrected deviation signal, means responsive to said first cyclic signal for providing a third signal having a predetermined magnitude and dwell time, means for averaging said third signal, means for obtaining a product signal of said averaged corrected deviation and third signals, means for multiplying said product signal by a constant signal having a magnitude determined by biologic segment electrical characteristics and placement of the electrodes thereon, thus obtaining a fourth signal, and means for multiplying said fourth signal by the tissue conductance signal, whereby an output signal is obtained indicative of flow rate of biologic fluid through the biologic segment.

2. A flow rate computer adjunct as in claim 1 wherein the artifact signal has a predetermined frequency and a residual noise level is contained in said corrected deviation signal related to the predetermined frequency, said means for averaging said corrected deviation signal including a resistor and a capacitor configured to provide a substantially DC output related to said corrected deviation signal, thereby reducing cyclic noise variation in the corrected deviation signal and allowing stabilization of said output signal for reading after a comparatively short period of time.

3. A flow rate computer adjunct as in claim 1 wherein said means responsive to said terminal portion of said second cyclic signal is a synchronous clamp adjusting said signal indicative of deviation to a level determined by said correction signal, whereby correction is made in said signal indicative of deviation during a pulsatile biologic fluid flow cycle for artifact signal magnitude in an immediately preceding cycle.

4. A flow rate computer adjunct as in claim 1 together with means for adjusting said signal proportional to tissue conductance thereby introducing bias and scale factor correction therein prior to obtaining said fourth signal.

5. A flow rate computer adjunct as in claim 1 together with scale factor amplifier means, and flow rate meter means for providing flow rate indication in desired units of volume per increment of time.

6. A flow rate computer adjunct as in claim 1 together with fixed value multiplier means and flow rate meter means for providing normalized flow rate indication in flow rate per volumetric unit of tissue in the biologic segment.

7. A flow rate computer adjunct for use with an impedance plethysmograph having electrodes applied to a thoracic segment having pulsatile biologic fluid flow therethrough, the impedance plethysmograph providing a signal indicative of deviation from the basic conductance of the thoracic segment, the signal indicative of deviation containing an artifact signal, comprising an artifact signal, comprising means for providing a first cyclic signal indicative of the pulsatile biologic fluid flow, means for receiving said first cyclic signal providing a second cyclic signal having an initial and a terminal portion, means responsive to said initial portion of said second cyclic signal for sensing the instantaneous magnitude of the artifact signal and producing a correction signal corresponding thereto, means responsive to said terminal portion of said second cyclic signal for applying said correction signal to the signal indicative of deviation thereby obtaining a corrected deviation signal, means for averaging said corrected deviation signal, means responsive to said first cyclic signal for providing a third signal having a predetermined magnitude and dwell time, means for averaging said third signal, means for obtaining a product signal of said average corrected deviation and third signals, and means for multiplying said product by a constant determined by the unit of volume of the thoracic segment and providing an output signal indicative of biologic fluid flow rate per unit of thoracic segment volume.

8. In the combination of an impedance plethysmograph and computer adjunct wherein said impedance plethysmograph includes first and second electrode pairs for application to a biologic segment experiencing pulsatile blood flow therethrough urged by heart pumping action and providing signals indicative of biologic segment conductance and deviation from basic segment resistance during pulsatile blood flow, wherein the deviation signal is subject to including breathing and movement artifacts therein, comprising means for providing a cyclic heart rate signal, means for receiving said heart rate signal providing a conditioned signal having a measuring portion and a correcting portion, means responsive to said measuring portion for measuring the instantaneous magnitude of the breathing and movement artifacts and producing a correction signal, means responsive to said correcting portion for applying said correction signal to the deviation signal thereby obtaining a corrected deviation signal, means for averaging said corrected deviation signal, means for receiving said heart rate signal providing a cyclic signal related thereto, means for averaging said cyclic signal, means for obtaining a product of said averaged corrected deviation and cyclic signals, first means for multiplying said product by a signal having a magnitude determined by biologic segment electrical characteristics and electrode pair placement and providing an adjusted product signal, and second means for multiplying said adjusted product signal and the signal indicative of biologic segment conductance, thereby providing an output signal related to blood flow rate in units of volume per unit of time through the biologic segment.

9. The method of determining hydraulic flow rate of body fluids through a body segment supplied with blood by a pulsing rate of the heart, comprising the steps of measuring the body segment conductance, measuring the deviation of the body segment resistance from a quiescent segment resistance wherein the deviation includes artifact signals therein, measuring the pulsing rate of the heart, measuring the instantaneous magnitude of the artifact signals each time the heart pulses and generating a correction signal related thereto, correcting the measurement deviation of the body segment resistance for artifact signal by connecting the correction signal thereto, averaging the corrected measurement of deviation of the body segment resistance, averaging the measurement of heart pulsing rate, multiplying the averaged measurements together to obtain a product signal, and multiplying the product signal by the measurement of body segment conductance, thereby producing an output signal indicative of blood flow rate through the body segment.

10. The method of claim 9 wherein the artifact signals have a predetermined frequency, and the step of averaging the corrected measurement of deviation comprises the steps of integrating the corrected measurement to provide a DC signal substantially free of noise due to signal variations at and above the predetermined frequency, and imposing a time characteristic in the output signal so that it is indicative of measured quantities within a shorter time period after occurrence thereof.

11. The method of determining the hydraulic flow rate of blood through a thoracic segment supplied by pulsing of the heart, comprising the steps of measuring the deviation of the thoracic segment resistance from a quiescent thoracic segment resistance wherein the deviation includes an artifact signal therein having a primary frequency, measuring the pulsing rate of the heart, measuring the instantaneous magnitude of the artifact signal each time the heart pulses, generating a correction signal related to the measured magnitude of the artifact signal, correcting the measurement of deviation of the thoracic segment resistance for artifact signal by connecting the correction signal thereto, averaging the corrected measurement of deviation of the body segment resistance, averaging the measurement of the pulsing rate of the heart, multiplying the averaged measurements together to obtain an output signal indicative of blood flow rate through the thoracic segment.

12. The method of claim 11 wherein the corrected measurement has a residual portion of the artifact signal therein, and the step of averaging the corrected measurement comprises the step of integrating the corrected measurement of the deviation of thoracic segment resistance, thereby obtaining a DC output indicative thereof, and imposing a time constant in the integrating step for obtaining blood flow rate indication shortly after the occurrance of the actual blood flow.

* * * * *